(12) United States Patent
Sukkau

(10) Patent No.: US 12,708,283 B2
(45) Date of Patent: Aug. 18, 2026

(54) APPARATUS AND METHOD FOR ACQUIRING A POSITION OF A REGION TO BE EXAMINED

(71) Applicant: Siemens Healthineers AG, Forchheim (DE)

(72) Inventor: Johann Sukkau, Herzogenaurach (DE)

(73) Assignee: Siemens Healthineers AG, Forchheim (DE)

( * ) Notice: Subject to any disclaimer, the term of this patent is extended or adjusted under 35 U.S.C. 154(b) by 160 days.

(21) Appl. No.: 18/783,689

(22) Filed: Jul. 25, 2024

(65) Prior Publication Data

US 2025/0031991 A1 Jan. 30, 2025

(30) Foreign Application Priority Data

Jul. 28, 2023 (EP) .................................... 23188478

(51) Int. Cl.
*A61B 5/055* (2006.01)
*A61B 5/00* (2006.01)

(52) U.S. Cl.
CPC ................ *A61B 5/055* (2013.01); *A61B 5/70* (2013.01); *A61B 5/742* (2013.01)

(58) Field of Classification Search
CPC ........... A61B 5/055; A61B 5/70; A61B 5/742; A61B 5/0033; A61B 5/7445; A61B 6/032; A61B 6/037; A61B 5/704; A61B 6/0487; A61B 5/0077; A61B 6/0492; A61B 6/469; G01R 33/283
See application file for complete search history.

(56) References Cited

U.S. PATENT DOCUMENTS 5,975,710 A * 11/1999 Luster .................. G02B 27/143 359/857
2002/0118280 A1* 8/2002 Medlar .................. H04N 7/181 348/E7.086

(Continued)

FOREIGN PATENT DOCUMENTS

DE 102012214283 A1 2/2014
DE 102021202978 A1 9/2022
EP 4212103 A1 * 7/2023 ............... G06T 7/60

OTHER PUBLICATIONS

Sukkau, J., “Methods for Improving Eye Safety When Using Laser and Video Projectors on MR Scanners”, Siemens AG, 2024.

*Primary Examiner* — Pascal M Bui Pho
*Assistant Examiner* — Nicholas A Robinson
(74) *Attorney, Agent, or Firm* — Banner & Witcoff, Ltd.

(57) ABSTRACT

The disclosure describes a medical imaging apparatus comprising a couch on which an object can be positioned for a medical imaging examination, a first acquisition apparatus which is embodied for acquiring a position of a region to be examined of the object, a projection apparatus which is embodied for a projection and/or display of a feedback marking at the acquired position of the region to be examined, a linear axis unit which comprises a drive unit for moving the projection apparatus, and a second acquisition apparatus, which is embodied to acquire position data of a medical operator during preparation of the object for the medical imaging examination, wherein the projection apparatus, using the acquired position data of the second acquisition apparatus, is tracked to a position of the medical operator in the longitudinal direction of the couch during preparation of the object.

20 Claims, 3 Drawing Sheets

(56) References Cited

U.S. PATENT DOCUMENTS

| | | | | |
|---|---|---|---|---|
| 2007/0030957 | A1* | 2/2007 | Pommi | G06T 7/73<br>378/197 |
| 2013/0274590 | A1* | 10/2013 | Auboiroux | A61B 90/361<br>600/411 |
| 2013/0342350 | A1* | 12/2013 | Popescu | G08B 21/02<br>340/573.1 |
| 2016/0113592 | A1* | 4/2016 | Murugappan | A61B 5/7285<br>600/413 |
| 2022/0125395 | A1* | 4/2022 | Burbar | A61B 6/037 |
| 2022/0304634 | A1 | 9/2022 | Sukkau et al. | |
| 2022/0365150 | A1* | 11/2022 | Weiss | G02B 5/0825 |

* cited by examiner

21: Gradient control unit
22: RF Antenna control unit
23: System control unit
25: Representation unit
26: Input unit
55: Computing unit 10
11
12
13
14
15
16
17
18
19
20
Z
21
22
23
24
25
26
27
28
29, 35
30
31
32
33
34
36
37
38
39, 40
41
52
53, 54
55
56

47
39, 40
44
51
51
49
48
50
50
46
41
41
45
15
11
32
33
43
42
19
16

APPARATUS AND METHOD FOR ACQUIRING A POSITION OF A REGION TO BE EXAMINED

CROSS-REFERENCE TO RELATED APPLICATIONS

The present application claims priority to and the benefit of European patent application no. EP 23188478.4, filed on Jul. 28, 2023, the contents of which are incorporated herein by reference in their entirety.

TECHNICAL FIELD

The present disclosure relates to a medical imaging apparatus with a couch on which an object can be positioned for a medical imaging examination and which can be moved into a recording region of the medical imaging apparatus, a first acquisition apparatus which is embodied for acquiring a position of a region to be examined of the object, a projection apparatus which is embodied for a projection and/or display of a feedback marking at the acquired position of the region to be examined, and a linear axis unit which comprises a drive unit for moving at least the marking apparatus, wherein the linear axis unit is arranged above the couch parallel to the longitudinal direction of the couch. Furthermore, the disclosure comprises a method for acquiring a position of a region to be examined of an object by means of a first acquisition apparatus for a medical imaging examination.

BACKGROUND

For a medical imaging examination, in particular a magnetic resonance examination, it is necessary for the patient, in particular a region to be examined of the patient, to be correctly positioned in the isocenter of the medical imaging apparatus. For example, the region to be examined of the patient is marked with a laser beam which is arranged on a front side of a magnetic resonance apparatus. For this, a couch, on which the patient is positioned for the magnetic resonance examination, has to be moved in the z-direction, which corresponds to the longitudinal direction of the couch, until the region to be examined of the patient coincides with the laser marking. Following the marking of the region to be examined the couch is automatically moved, together with the patient, into a recording region of the magnetic resonance apparatus, with the region to be examined or the marked region of the patient being positioned in the isocenter. A positioning of this kind is very difficult for an inexperienced and/or unpracticed user, however, so the positioning requires a great deal of time and/or incorrect positionings can also occur.

From DE 10 2021 202 978 A1, an apparatus for acquiring and marking a region to be examined of a patient is known, wherein the apparatus is arranged on a ceiling above the couch. In this connection, the region to be examined is marked by a user with a marker object and is acquired by an acquisition apparatus. A feedback marking at the acquired position is then projected by means of a projection apparatus. If the position of the feedback marking coincides with the position of the marker object a shift of the couch in the direction of the isocenter is ascertained using this position. However, this method has the drawback that the projection apparatus is only tracked to the corresponding position after acquisition of the marker object. This tracking can take a few seconds, and this results in low acceptance among users.

SUMMARY

The present disclosure is based on the object of enabling simple and fast marking of the region to be examined. The object is achieved by the features of the embodiments as described herein, including the claims.

The disclosure starts from a medical imaging apparatus comprising:

- a couch on which an object can be positioned for a medical imaging examination and which can be moved into a recording region of the medical imaging apparatus,
- a first acquisition apparatus which is embodied for acquiring a position of a region to be examined of the object for a medical imaging examination,
- a projection apparatus which is embodied for a projection and/or display of a feedback marking at the acquired position of the region to be examined,
- a linear axis unit which comprises a drive unit for moving the projection apparatus, wherein the linear axis unit is arranged above the couch parallel to the longitudinal direction of the couch.

Inventively, the medical imaging apparatus has a second acquisition apparatus which is embodied to acquire position data of a medical operator during preparation of the object for the medical imaging examination, wherein the projection apparatus, using the acquired position data of the second acquisition apparatus, is tracked to a position of the medical operator relative to a longitudinal direction of the couch on the linear axis unit during preparation of the object.

The medical imaging apparatus can comprise a computed tomography apparatus (CT apparatus), a PET apparatus (positron emission tomography apparatus), a magnetic resonance apparatus (e.g. an MRI device), or a combination of a plurality of medical imaging apparatuses, such as a magnetic resonance PET apparatus or a CT-PET apparatus.

The medical imaging apparatus may be for instance configured and/or embodied to acquire medical and/or diagnostic image data of a patient and/or object.

The medical imaging apparatus may e.g. comprise a scanner unit for acquiring the medical and/or diagnostic image data. The scanner unit surrounds a recording region of the medical imaging apparatus. The recording region may e.g. be cylindrical and embodied for recording the patient and/or the object, e.g. the region to be examined of the patient and/or object, for a medical imaging examination.

The object to be examined may e.g. comprise a patient. As an example, a clinical and/diagnostic problem on the patient is to be clarified by means of the medical imaging examination. In addition, the object can also comprise a phantom for, by way of example, adjusting measurements and/or further objects that appear expedient to a person skilled in the art.

For a medical imaging examination, the object, e.g. the patient or the region to be examined of the object, e.g. of the patient, is positioned inside the recording region of the medical imaging apparatus. The field of view (FOV) and/or an isocenter of the medical imaging apparatus may be arranged inside the recording region. The FOV may comprise an acquisition region of the medical imaging apparatus, inside of which region the conditions for acquiring medical image data inside the recording region exist, such as a homogeneous basic magnetic field in the case of an embodiment of the medical imaging apparatus as a magnetic resonance apparatus. The isocenter of the medical imaging apparatus may comprise the region and/or point inside of the magnetic resonance apparatus, which has the optimum and/or ideal conditions for acquiring medical image data. For example, in the case of an embodiment of the medical imaging apparatus as a magnetic resonance apparatus, the isocenter comprises the most homogeneous magnetic field region inside the magnetic resonance apparatus.

For moving and/or positioning the object and/or the patient, e.g. the region to be examined of the object and/or of the patient, inside the recording region the medical imaging apparatus comprises a patient-supporting apparatus. The patient-supporting apparatus has a couch, with the couch being embodied to be movable relative to the scanner unit. In this connection the couch may be embodied to be movable inside the recording region in the longitudinal direction of the couch and/or in the longitudinal direction of the recording region to position the patient in an examination position inside the recording region.

The first acquisition apparatus is embodied to acquire a position of the region to be examined of the object, e.g. of the patient, for a pending medical imaging examination. The first acquisition apparatus can comprise a camera, for example a 2D camera or a 3D camera. In addition, the first acquisition apparatus can also comprise more than one camera, for example a camera array. If the first acquisition apparatus comprises a camera, it can be arranged, for example, on a ceiling of an examination space in which the medical imaging apparatus is arranged. As an example, the first acquisition apparatus is arranged in a front region in front of a front side of the scanner unit. The front region is located in front of the scanner unit so as to adjoin the front side. In addition, the acquisition apparatus can comprise further units and/or sensors for acquiring the region to be examined, and these can be arranged, for example, on the couch.

In order to acquire the region to be examined, the user may position a marker element on the region to be examined of the object and/or the patient, with the marker element being identified as such by the first acquisition apparatus and its position being acquired. The marker element can comprise, for example, a finger of the medical operator or also a hand-guided item, for example a marker bar.

The projection apparatus may e.g. comprise a video projector and/or a laser-marking unit, which is embodied for projection and/or display of a feedback marking at the position of the region to be examined acquired by the first acquisition apparatus. By means of the feedback marking, the user receives feedback as to whether the region to be examined of the object and/or the patient was correctly acquired.

The linear axis unit may e.g. comprise a drive unit and a rail, with at least the projection apparatus being automatically positioned and/or shifted on the rail by means of the drive unit. The linear axis unit, together with the projection apparatus, may be arranged on a ceiling of the examination space. As an example, the linear axis unit may be arranged on the ceiling of the examination space in such a way that the couch, which during a preparation is arranged in a front region in front of a front side of the scanner unit, is located in a projection field of the projection apparatus. As an example, the linear axis unit, together with the projection apparatus, may also arranged in this front region in front of the scanner unit. The linear axis unit can comprise a computing unit, moreover, with the computing unit determining a position along the rail for the projection apparatus using the acquired position data of the first acquisition apparatus. A drive moment for a movement of the projection apparatus on the rail may be generated by means of the drive unit. In this connection the rail may be oriented parallel to the longitudinal direction of the couch.

DE 10 2021 202 978 A1 discloses a detailed description of the first acquisition apparatus, the projection apparatus and the linear axis unit, with reference to DE 10 2021 202 978 A1 being made herewith.

The second acquisition apparatus is designed for acquiring position data of the medical operator during a preparation of the object for the pending medical imaging examination. The preparation of the object comprises a positioning of the object, for example of the patient, on the couch. In addition, preparing the object can also comprise attaching supplementary units to the object, such as a positioning of support pillows on the object and/or a positioning of local magnetic resonance coils which are arranged around the region to be examined of the object, e.g. of the patient, and/or attaching a unit for acquiring physiological signals, for example an ECG unit, etc. In an embodiment, position data of the medical operator is continuously acquired throughout the entire preparation of the object, e.g., of the patient, until the preparation of the object for the pending medical imaging examination is complete.

In an embodiment, an item of position information of the medical operator is ascertained using the acquired position data. For instance, the item of position information of the medical operator comprises an item of position information relative to the z-direction of the scanner unit and/or the longitudinal direction of the couch.

A position is determined for the projection apparatus using the acquired position data, e.g. using the ascertained item of position information of the medical operator, relative to the longitudinal direction of the couch. The projection apparatus is then shifted and/or moved to this position, e.g. by means of the linear axis unit. As an example, the projection apparatus is shifted and/or moved in the longitudinal direction of the couch, which is parallel to the z-direction, by means of the linear axis unit. The position to which the projection apparatus is moved and/or tracked substantially corresponds to the position which was acquired by the second acquisition apparatus as the position of the medical operator. The position of the projection apparatus into which it is shifted can deviate by up to ±10 cm from the acquired position of the medical operator. The position of the projection apparatus into which it is shifted can deviate by up to ±20 cm from the acquired position of the medical operator. The position of the projection apparatus into which it is shifted can deviate by up to ±30 cm from the acquired position of the medical operator.

In addition, it can also be that, apart from the projection apparatus, the first acquisition apparatus is also tracked using the acquired position data of the second acquisition apparatus, to a position of the medical operator in the z-direction on the linear axis unit during the preparation of the object. As an alternative to tracking the first acquisition apparatus, it can also be permanently arranged on the ceiling of the examination space, for example in the case of an embodiment as a high-resolution camera, e.g. a 3D camera.

In this way, the projection apparatus can always be arranged in the vicinity of the medical operator in the longitudinal direction of the couch, so with placement of the marker element for defining and/or acquiring the region to be examined of the object, e.g. of the patient, the projection apparatus only has a short traverse path or is already arranged at the position of the region to be examined in the longitudinal direction of the couch. The projection apparatus can hereby be brought and/or moved particularly quickly and expeditiously into the position in which a feedback marking is to be projected. The medical operator can thereby also receive the feedback marking particularly promptly. This enables simple and fast marking of the region to be examined, for example, so a workflow of the medical operator is not delayed by long waiting times. For example, and accidental termination of acquisition of the region to be examined due to a removal of the marker element from the region to be examined by the medical operator can also be reduced and/or prevented hereby.

In addition, a selection can be made using the continuously acquired position data of the medical operator by means of the second acquisition apparatus as to whether the first acquisition apparatus has to be switched on or not for a detection and/or acquisition of a marker element. Resources, such as a CPU time and/or energy consumption, can be saved hereby. A further advantage is that the first acquisition apparatus does not require any special and/or cost-intensive EMC measures (measures relating to electromagnetic compatibility) hereby, such as a special shielding housing in the case of an embodiment of the medical imaging apparatus as a magnetic resonance apparatus, since it is switched off in the critical magnetic resonance measuring time.

In an advantageous development of the medical imaging apparatus, it can be provided that the medical imaging apparatus is embodied as a magnetic resonance apparatus. For instance, in the case of magnetic resonance examinations which take up a relatively long time, an exact positioning is particularly important. The time a patient spends inside the recording region is thereby also reduced to the measuring time and repeated measurements due to incorrect positionings can thus be prevented.

The magnetic resonance apparatus may for instance comprise a scanner unit, embodied as a magnetic unit, for acquiring the medical and/or diagnostic image data. The magnetic unit comprises a basic magnet, a gradient coil unit and a radio-frequency antenna unit. The radio-frequency antenna unit may be permanently arranged inside the magnetic unit. The magnetic unit surrounds a recording region of the magnetic resonance apparatus. The recording region may be e.g. cylindrical and is embodied for a recording of the patient and/or of the object, for example of the region to be examined of the patient and/or object, for a magnetic resonance examination.

The basic magnet is embodied for generating a homogeneous basic magnetic field with a defined magnetic field strength, such as with a magnetic field strength of 0.55 T or 1.5 T or 3 T or 7 T, etc. For sentence, the basic magnet is embodied for generating a strong, constant, and homogeneous basic magnetic field. The gradient system is embodied for generating magnetic field gradients which are used for a spatial encoding during an imaging. The radio-frequency antenna unit is embodied for emitting radio-frequency pulses and/or excitation pulses for generating magnetic resonance signals.

In an advantageous development of the medical imaging apparatus, it can be provided that the second acquisition apparatus comprises a sensor unit for acquiring the position data of the medical operator, wherein the sensor unit has a field of view which comprises a region next to the couch. The sensor unit can comprise a camera and/or a thermal imaging camera and/or further sensor units that appear expedient to a person skilled in the art. During preparation of the object, e.g. of a patient, for the pending medical imaging examination, the couch is located in the front region in front of the front side of the scanner unit. The region next to the couch may comprise a region of the medical operator in which they stay for a preparation of the object, e.g. of a patient, for a medical imaging examination. Simple and direct acquisition of the position data of the medical operator during a preparation of the object, e.g. of a patient, can advantageously be achieved in this way for a medical imaging examination. In addition, acquisition of the position data of the medical operator independently of the acquisition of the region to be examined can be provided.

In an advantageous development of the medical imaging apparatus, it can be provided that the sensor unit comprises at least one thermal imaging sensor. In an embodiment, the sensor unit comprises a thermal imaging sensor array with two or more thermal imaging sensors. The individual thermal imaging sensors may comprise infrared sensors that are embodied for acquiring thermal radiation, e.g. infrared radiation. The use of thermal imaging sensors can provide reliable and robust identification of the medical operator for acquiring the position data of the medical operator. In addition, the sensor unit for acquiring the position data of the medical operator can be particularly favorably embodied. Acquisition of the position data of the medical operator with a camera, for example the camera of the first acquisition apparatus, requires laborious image reconstruction and analysis to identify the medical operator, and this is much easier by means of the thermal imaging sensors. As an example, energy and/or computing power and/or acquisition time can be saved in this way.

In an advantageous development of the medical imaging apparatus, it can be provided that the second acquisition apparatus comprises a field of view manipulation unit, which is embodied to fade out a region of the couch from the field of view of the sensor unit. The field of view manipulation unit can comprise a diaphragm and/or a mirror system with at least one mirror, which divert and/or restrict the field of view of the sensor unit in such a way that the region of the couch is not encompassed by the field of view of the sensor unit. In this way, thermal radiation of a patient located on the couch can be easily faded out during acquisition of the position data of the medical operator. For instance, an acquired thermal radiation can be clearly and directly associated with the medical operator in this way when evaluating the position data acquired by means of the second acquisition apparatus and errors can be reduced and/or eliminated during evaluation.

In an advantageous development of the medical imaging apparatus, it can be provided that the field of view manipulation unit is embodied for dividing and/or deflecting the field of view of the sensor unit into two partial fields of view. In an embodiment, each partial field of view covers a region next to the couch, wherein the two partial fields of view are arranged at different regions next to the couch. A first partial field of view can cover the region on the right of the couch and a second partial field of view the region on the left of the couch, with a central region, e.g. the region of the couch, being excluded from the field of view of the sensor unit. In this way, a patient positioned on the couch can be easily eliminated from the field of view of the sensor unit. In addition, each of the two partial fields of view can advantageously be embodied to be large enough to localize the medical operator. For instance, both regions next to the couch can be acquired in this way by means of a single sensor unit for a localization of the medical operator.

In an advantageous development of the medical imaging apparatus, it can be provided that the field of view manipulation unit comprises a mirror system with two acquisition paths, wherein each acquisition path has at least one mirror for diverting a partial field of view. In an embodiment, one partial field of view respectively is directed by the sensor unit onto the at least one mirror and by the at least one mirror onto the region next to the couch. For example, the mirror system may have two mirrors for each acquisition path, with one partial field of view respectively being deflected by the sensor unit onto a first mirror, by the first mirror onto a second mirror and by the second mirror onto the region next to the couch. In this way, the region of the couch can be excluded from the field of view of the sensor unit particularly easily. A further advantage of this embodiment is that acquisition of the two partial fields of view by means of the mirror system is much more favorable than equipping the second acquisition apparatus with a second thermal imaging sensor for dividing the field of view into two partial fields of view.

In an advantageous development of the medical imaging apparatus, it can be provided that the second acquisition apparatus has an evaluation unit which is embodied for an evaluation of the acquired position data. The evaluation unit may comprise a microcontroller. In addition, the evaluation unit may comprise software which is embodied for an evaluation of the position data acquired by means of the sensor unit, e.g. of the at least one thermal imaging sensor. In an embodiment, an item of position information of the medical operator in the z-direction and/or relative to the longitudinal direction of the couch is ascertained and/or determined by the evaluation unit, e.g. the microcontroller, when evaluating the position data acquired by means of the sensor unit. In this way, a direct and simple evaluation can be provided for a localization and/or a determination of the item of position information of the medical operator. As an example, the position data acquired by means of the sensor unit can in this way be evaluated independently of determining and/or defining the region to be examined.

In an advantageous development of the medical imaging apparatus, it can be provided that the second acquisition apparatus comprises a shielding housing. In an embodiment, the shielding housing comprises an EMC (electromagnetic compatibility)-safe shielding housing, which shields electromagnetic radiation from the second acquisition apparatus and/or shields electromagnetic radiation of the second acquisition apparatus from the scanner unit, e.g. a magnetic unit of a magnetic resonance apparatus. In this way, an undesirable interaction between the second acquisition apparatus and the scanner unit, e.g. the magnetic unit, can be advantageously prevented. For instance, trouble-free operation of the second acquisition apparatus and the scanner unit, e.g. of the magnetic unit, can be guaranteed.

In an advantageous development of the medical imaging apparatus, it can be provided that the second acquisition apparatus an optical data transfer unit for transferring an item of position information of the medical operator to the medical imaging apparatus and/or to the linear axis unit. The optical data transfer unit may for instance have at least one optical fiber for data transfer. In addition, the second acquisition apparatus, e.g. the evaluation unit of the second acquisition apparatus, may have a corresponding optical data interface. Undesirable interference of the medical imaging, for example undesirable artifacts in the medical image data, can be prevented by data transfer by means of the optical data transfer unit, e.g. the at least one optical fiber.

Furthermore, the disclosure includes a method for acquiring a position of a region to be examined of an object by means of a first acquisition apparatus for a medical imaging examination, comprising the following method steps:

preparing the object on a couch which can be moved in a recording region of a medical imaging apparatus, wherein the object is prepared manually by a medical operator, acquiring position data of the medical operator by means of a second acquisition apparatus during positioning of the object, tracking a projection apparatus in the longitudinal direction of the couch to a position of the medical operator, wherein the tracking takes place on the basis of an item of position information of the medical operator ascertained using the acquired position data, repeating the method steps of positioning the object, of acquiring the position data of the medical operator and the method step of tracking the projection apparatus until the region to be examined of the object is defined by means of manual positioning of a marker element, acquiring the position of the marker element by means of the first acquisition apparatus, and projection and/or display of a feedback marking by a projection apparatus at the acquired position of the region to be examined of the object.

A detailed description of acquiring the position of the marker element and a projection and/or display of a feedback marking is disclosed in DE 10 2021 202 978 A1, with reference hereby being made to DE 10 2021 202 978 A1.

The projection apparatus may be tracked by means of the linear axis unit of the medical imaging apparatus.

The projection and/or display of a feedback marking also comprises a positioning of the projection apparatus at the position of the marker element relative to the longitudinal direction of the couch.

In this way, the projection apparatus can always be arranged in the vicinity of the medical operator in the longitudinal direction of the couch, so with placement of the marker element for defining and/or acquiring the region to be examined of the object, e.g. of the patient, the projection apparatus only has a short traverse path or is already arranged at the position of the region to be examined in the longitudinal direction of the couch. The projection apparatus can hereby be brought and/or moved particularly quickly and expeditiously into the position in which a feedback marking is to be projected. The medical operator can thereby also receive the feedback marking particularly promptly. This enables simple and fast marking of the region to be examined, e.g., so a workflow of the medical operator is not delayed by long waiting times. As an example, an accidental termination of acquisition of the region to be examined due to a removal of the marker element from the region to be examined by the medical operator can also be reduced and/or prevented hereby.

In addition, a selection can be made using the continuously acquired position data of the medical operator by means of the second acquisition apparatus as to whether the first acquisition apparatus has to be switched on or not for a detection and/or acquisition of a marker element. Resources, such as a CPU time and/or energy consumption, can be saved hereby. A further advantage is that the first acquisition apparatus does not require any special and/or cost-intensive EMC measures (measures relating to electromagnetic compatibility) hereby, such as a special shielding housing in the case of an embodiment of the medical imaging apparatus as a magnetic resonance apparatus, since it is switched off in the critical magnetic resonance measuring time.

The advantages of the method for acquiring a position of a region to be examined of an object by means of a first acquisition apparatus for a medical imaging apparatus substantially correspond to the advantages of the medical imaging apparatus which have been stated above in detail. Features, advantages or alternative embodiments mentioned in this connection can similarly be transferred to the other claimed subject matters, and vice versa.

In an advantageous development of the method, it can be provided that a region of the couch is faded out for acquiring the position data of the medical operator in the field of view of the second acquisition apparatus. In this way, thermal radiation of a patient located on the couch can be easily faded out during acquisition of the position data of the medical operator. If the second acquisition apparatus comprises a thermal imaging sensor, an acquired thermal radiation can be clearly and directly associated with the medical operator, moreover, during an evaluation of the position data acquired by means of the second acquisition apparatus and errors can be reduced and/or eliminated during the evaluation.

In an advantageous development of the method, it can be provided that a field of view of the second acquisition apparatus is divided and/or deflected for acquiring the position data of the medical operator. For this, the second acquisition apparatus has a field of view manipulation unit which divides and/or deflects the field of view. In an embodiment, the second acquisition apparatus, e.g. the field of view manipulation unit, has a mirror system which is embodied to divide and/or deflect the field of view into two partial fields of view. In an embodiment, each partial field of view covers a region next to the couch. A first partial field of view can cover the region on the right of the couch and a second partial field of view the region on the left of the couch, with a central region, e.g. the region of the couch, being excluded from the field of view of the sensor unit. In this way, a patient positioned on the couch can be easily faded out and/or eliminated from the field of view of the sensor unit. In addition, each of the two partial fields of view can advantageously be embodied to be large enough to localize the medical operator. For example, both regions next to the couch can be acquired in this way by means of a single sensor unit for a localization and acquisition of the position data of the medical operator.

In an advantageous development of the method, it can be provided that the acquired position data is evaluated by means of the second acquisition apparatus and an ascertained item of position information of the medical operator is transferred to a linear axis unit by means of an optical data transfer unit for the positioning of the projection apparatus. In an embodiment, the second acquisition apparatus comprises an evaluation unit, such as a microcontroller. The evaluation unit, e.g. the microcontroller, can comprise a corresponding optical data interface for a data transfer. The optical data transfer unit may comprise at least one optical fiber for data transfer to the linear axis unit and/or the medical imaging apparatus. In this way, the acquired position data can be directly evaluated. In addition, undesirable interference of the medical imaging, for example undesirable artifacts in the medical imaging data, can be prevented by the data transfer by means of optical fiber.

In an advantageous development of the method, it can be provided that an examination position of the couch is calculated using the acquired position of the region to be examined of the object. The examination position of the couch is calculated by means of a computing unit and/or control unit of the medical imaging apparatus. The examination position comprises that position of the couch in respect of the scanner unit such that the region to be examined of the object, e.g. of the patient, is arranged within the isocenter of the medical imaging apparatus. This enables simple and time-saving positioning of the region to be examined in the isocenter of the medical imaging apparatus. For example, the medical operator can advantageously be assisted in this way with the positioning of a patient inside the medical imaging apparatus and a positioning workflow can be simplified for inexperienced users.

In an advantageous development of the method, it can be provided that the couch is automatically moved into the examination position for acquiring medical imaging data of the region to be examined of the object. This can likewise enable simple and time-saving positioning of the region to be examined in the isocenter of the medical imaging apparatus. For this the patient-supporting apparatus may have a corresponding horizontal adjusting unit and a position control unit in order to position the couch in the examination position.

Furthermore, the disclosure includes a computer program product, which comprises a program and can be directly loaded into a memory of a programmable control unit, with program means to execute a method for acquiring a position of a region to be examined of an object by means of a first acquisition apparatus for a medical imaging examination when the program is executed in the control unit. The computer program potentially requires program means, for example libraries and auxiliary functions, in order to implement the corresponding embodiments of the method. The computer program can comprise software with a source code which still has to be compiled and linked or which only has to be interpreted, or an executable software code which just has to be loaded into a corresponding computing unit for execution.

The computer program product can be loaded directly into a memory of a programmable computing unit and has program code means to execute a method when the computer program product is executed in the computing unit. The computer program product can be a computer program or comprise a computer program. The method can consequently be executed quickly, in an identically repeatable manner and robustly. The computer program product is configured in such a way that it can execute the inventive method steps by means of the computing unit. The computing unit must in each case have the requirements, such as an appropriate main memory, an appropriate graphics card or an appropriate logic unit, so the respective method steps can be efficiently executed. The computer program product is saved, for example, on a computer-readable medium or stored on a network or server from where it can be loaded into the processor of a local computing unit which can be directly connected to the medical imaging apparatus or can be embodied as part of it. Furthermore, items of control information of the computer program product can be saved on an electronically readable data carrier. The items of control information of the electronically readable data carrier can be embodied in such a way that they execute an inventive method when the data carrier is used in a computing unit. The computer program product can thus also constitute the electronically readable data carrier. Examples of electronically readable data carriers are a DVD, a magnetic tape, a hard disk or a USB stick on which electronically readable items of control information, e.g. software (cf. above), is saved. When these items of control information (software) are read from the data carrier and saved in a controller and/or computing unit, all embodiments of the above-described method can be carried out. The disclosure can thus also start from said computer-readable medium and/or said electronically readable data carrier.

BRIEF DESCRIPTION OF THE DRAWINGS

Further advantages, features and details of the disclosure can be found in the exemplary embodiment described below and on the basis of the drawings.

In the drawings.

DETAILED DESCRIPTION OF THE DISCLOSURE

Figure 1:
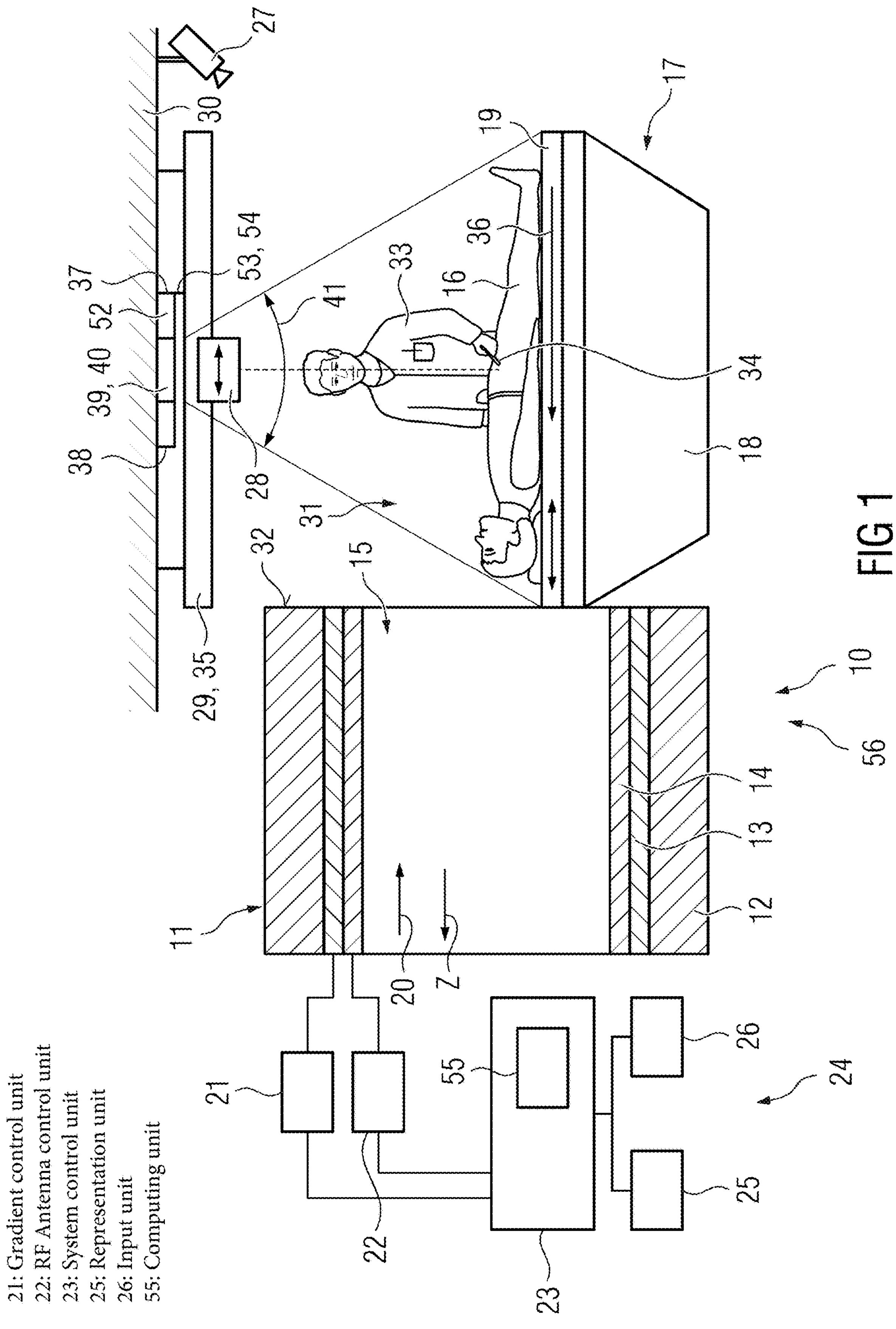
FIG. 1 illustrates an example medical imaging apparatus embodied as a magnetic resonance apparatus in a schematic representation, in accordance with one or more aspects of the present disclosure.

FIG. 1 schematically represents a medical imaging apparatus 56. In the present exemplary embodiment, the medical imaging apparatus 56 is formed by a magnetic resonance apparatus 11, with the present disclosure being explained, by way of example, on the basis of the magnetic resonance apparatus. The present disclosure is not limited to an embodiment of the medical imaging apparatus 56 to a magnetic resonance apparatus 11, however, and further embodiments of the medical imaging apparatus 56 are conceivable at any time.

The magnetic resonance apparatus 10 comprises a scanner unit, embodied as a magnetic unit 11, with a basic magnet 12, a gradient coil unit 13, and a radio-frequency antenna unit 14. In addition, the medical imaging apparatus 56, e.g. the magnetic resonance apparatus 10, has a recording region 15 for recording an object and/or patient 16 for a magnetic resonance examination. In the present exemplary embodiment, the recording region 15 is cylindrical and cylindrically surrounded in a circumferential direction by the magnetic unit 11. Basically, a different embodiment of the recording region 15 is conceivable at any time, however.

The medical imaging apparatus 56, e.g. the magnetic resonance apparatus 10, has a patient-supporting apparatus 17 for positioning the object and/or patient 16, e.g. a region to be examined of the patient 16, inside the recording region 15. The patient-supporting apparatus 17 has a base unit 18 and a couch 19, which can move in respect of the base unit 18. The couch 19 is embodied so it can move inside the recording region 15 for positioning of the object and/or patient 16, e.g. the region to be examined of the patient 16. In an embodiment, the couch 19 is movably mounted in the direction of a longitudinal extension of the recording region 15 and/or in the z-direction.

The basic magnet 12 of the magnetic unit 11 is embodied for generating a strong and constant basic magnetic field 20. The basic magnet 12 can be embodied, for example, as a superconducting basic magnet 12 or also as a permanent magnet. The gradient coil unit 13 of the magnetic unit 11 is embodied to generate magnetic field gradients, which are used for spatial encoding during imaging. The gradient coil unit 13 is controlled by means of a gradient control unit 21 of the magnetic resonance apparatus 10. The radio-frequency antenna unit 14 of the magnetic unit 11 is embodied to excite a polarization which is established in the basic magnetic field 20 generated by the basic magnet 12. The radio-frequency antenna unit 14 is controlled by a radio-frequency antenna control unit 22 of the magnetic resonance apparatus 10 and irradiates radio-frequency magnetic resonance sequences into the recording region 15 of the magnetic resonance apparatus 10.

The magnetic resonance apparatus 10 has a system control unit 23 for controlling the basic magnet 12, the gradient control unit 21 and for controlling the radio-frequency antenna control unit 22. The system control unit 23 centrally controls the magnetic resonance apparatus 10, such as carrying out a predetermined imaging gradient echo sequence. In addition, the system control unit 23 comprises an evaluation unit (not represented) for an evaluation of medical image data which is acquired during the magnetic resonance examination.

Furthermore, the medical imaging apparatus 56, e.g. the magnetic resonance apparatus 10, comprises a user interface 24, which is connected to the system control unit 23. Items of control information such as imaging parameters, as well as reconstructed magnetic resonance images, can be displayed for a medical operator 33 on a representation unit 25, for example on at least one monitor, of the user interface 24. Furthermore, the user interface 24 has an input unit 26 by means of which items of information and/or parameters can be input by a medical operator 33 during a measuring process.

The medical imaging apparatus 56, e.g. the magnetic resonance apparatus 10, has a first acquisition apparatus (also referred to herein as first acquisition circuitry) 27, a projection apparatus (also referred to herein a projector) 28 and a linear axis unit 29 (also referred to herein as a linear axis positioner) for positioning the patient 16. The first acquisition apparatus 27 is embodied for acquiring a position of a region to be examined of the object and/or of the patient 16 for a magnetic resonance examination. For this the first acquisition apparatus 27 may comprise a camera, such as a 2D camera and/or a 3D camera. In the present exemplary embodiment, the first acquisition apparatus 27 is arranged on a ceiling 30 of the examination space in which the magnetic unit 11 is arranged. The first acquisition apparatus 27 is arranged in a front region 31 in front of a front side 32 of the magnetic unit 11 to acquire the patient 16 and/or the couch 19 before being moved into the recording region 15.

The medical operator 33 may position a marker element 34 at the region to be examined, which element is identified and acquired by the first acquisition apparatus 27, for acquiring the region to be examined. The marker element 34 can comprise, for example, a finger of the medical operator 33 or also a hand-guided item, for example a marker bar.

The projection apparatus 28 may comprise a video projector and/or a laser marking unit, which is embodied for a projection and/or display of a feedback marking at the position acquired by the first acquisition apparatus 27. The feedback marking is provided for the user, e.g. the medical operator 33, to check a position of the region to be examined acquired by the first acquisition apparatus 27.

The linear axis unit 29 may for instance be arranged on the ceiling 30 of the examination space. In an embodiment, the linear axis unit 29 is arranged on the ceiling 30 of the examination space in such a way that the couch 19, which during a preparation is arranged in the front region 31 in front of the front side 32 of the magnetic unit 11, is located in a projection field of the projection apparatus 28. As an example, the linear axis unit 29, together with the projection apparatus 28, may also be arranged in the front region 31 in front of the front side 32 of the magnetic unit 11. The linear axis unit 29 may comprise for instance a drive unit (not represented) and a rail 35, with the projection apparatus 28 being automatically positioned and/or shifted on the rail 35 by means of the drive unit. The linear axis unit 29 can comprise a computing unit, moreover, which determines a position along the rail 35 for the projection apparatus 28 for a projection of the feedback marking using the acquired position data of the first acquisition apparatus 27. The rail 35 may for instance be oriented parallel to the longitudinal direction 36 of the couch 19.

The medical imaging apparatus 56, e.g. the magnetic resonance apparatus 10, also has a second acquisition apparatus (also referred to herein as second acquisition circuitry) 37 which is embodied for acquiring position data of the medical operator 33 during a preparation of the object, e.g. of the patient 16, for the magnetic resonance examination. The acquired position data is used to track the projection apparatus 28 on the linear axis unit 29 to a position of the medical operator 33 in the longitudinal direction 36 of the couch 19 during preparation of the object and/or of the patient 16. A position for the projection apparatus 28 is determined and the projection apparatus 28 is shifted and/or moved to this position, e.g. by means of the linear axis unit 29, using the acquired position data, e.g. on the basis of the ascertained position in the longitudinal direction 36 of the couch 19. The position to which the projection apparatus 28 is moved and/or tracked substantially corresponds to the position which was acquired by the second acquisition apparatus 37 as the position of the medical operator 33. The position of the projection apparatus 28 into which it is shifted can deviate by up to any suitable range such as for instance ±10 cm, ±20 cm, ±30 cm, etc. from the acquired position of the medical operator 33.

The second acquisition apparatus 37 is arranged the ceiling 30 of the examination space. In addition, the second acquisition apparatus 37 has a shielding housing 38 inside which a sensor unit 39 for acquiring the position data of the medical operator 33 is arranged. The shielding housing 38 may comprise an EMC-proof shielding housing, which shields an electromagnetic radiation from the second acquisition apparatus 37.

The second acquisition apparatus 37 has the sensor unit (also referred to herein a sensor) 39 for acquiring the position of the medical operator 33. In the present exemplary embodiment, the sensor unit 39 comprises at least one thermal imaging sensor 40. In an embodiment, the sensor unit 39 comprises a thermal imaging sensor array with two or more thermal imaging sensors 40. The individual thermal imaging sensors 40 may for instance comprise infrared sensors which are embodied for acquiring thermal radiation, e.g. infrared radiation. In an alternative embodiment of the second acquisition apparatus 37, it can also comprise a camera and/or further sensor units 39 that appear expedient to a person skilled in the art.

Figure 2:
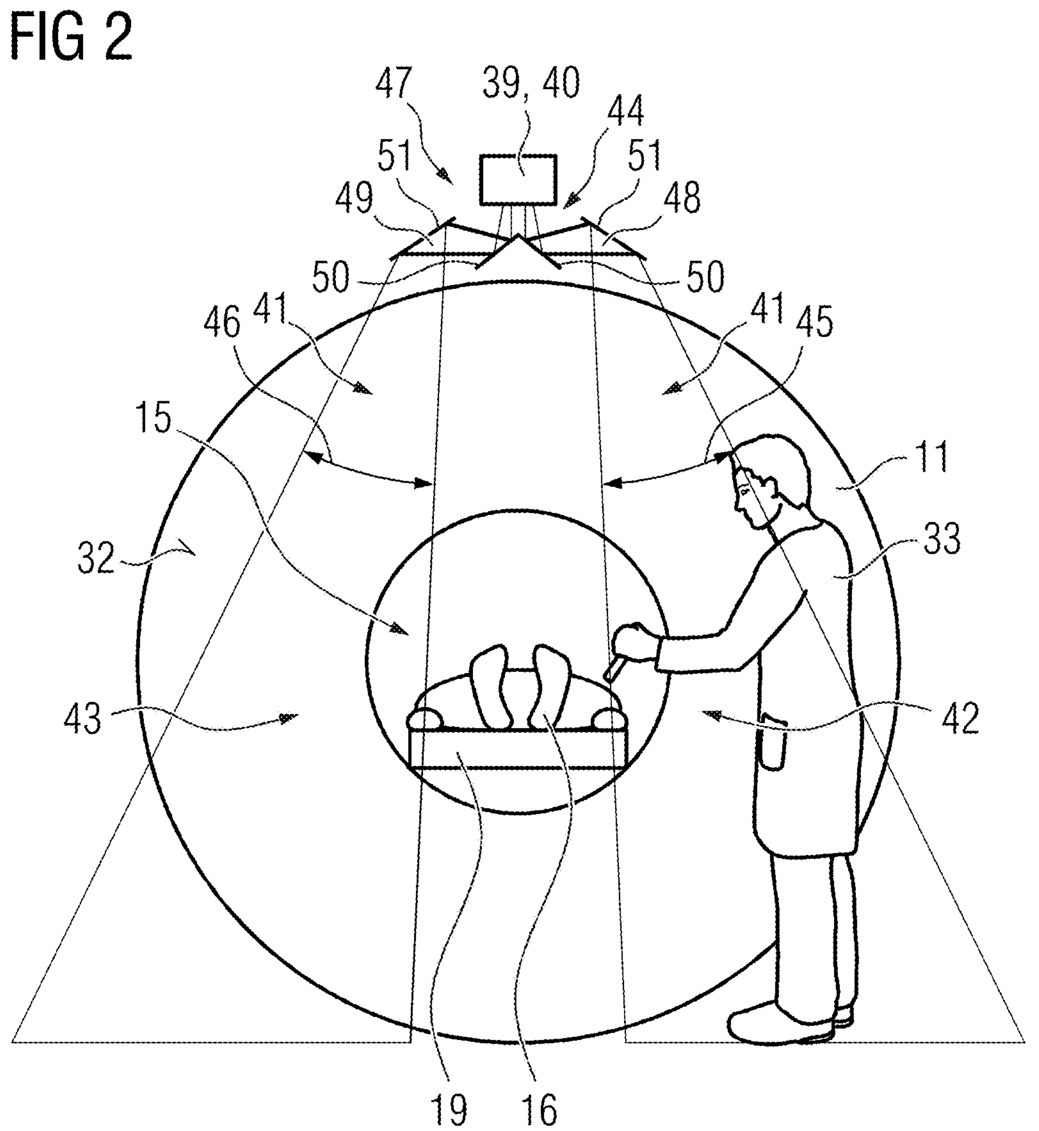
FIG. 2 illustrates an example second acquisition apparatus of the magnetic resonance apparatus, in accordance with one or more aspects of the present disclosure.

The sensor unit 39 has a field of view 41 which comprises a region 42, 43 next to the couch 19 on which the object, e.g. the patient 16, is positioned. The second acquisition apparatus 37 also has a field of view manipulation unit (also referred to herein as field of view manipulation circuitry) 44 which is embodied to fade out and/or eliminate a region of the couch 19 from the field of view 41 of the sensor unit 39, as is represented in FIG. 2. The field of view manipulation unit 44 is embodied to divide and/or deflect the field of view 41 of the sensor unit 39 into two partial fields of view 45, 46. In an embodiment, a first partial field of view 45 comprises a region 42 on the right next to the patient-supporting apparatus 17, e.g. the couch 19 of the patient-supporting apparatus 17. In addition, a second partial field of view 46 comprises a region 43 on the left next to the patient-supporting apparatus 17, e.g. the couch 19 of the patient-supporting apparatus 17.

For dividing and/or deflecting the field of view 41 of the sensor unit 39 the field of view manipulation unit 44 has a mirror system 47 with two acquisition paths 48, 49, with each acquisition path 48, 49 comprising at least one mirror 50, 51 for deflecting a partial field of view 45, 46. In the present exemplary embodiment, each acquisition path 48, 49 of the mirror system 47 has two mirrors 50, 51 for deflecting a partial field of view 45, 46. The partial field of view 45, 46 of the sensor unit 39 is respectively deflected onto the first mirror 50, from the first mirror 50 onto the second mirror 51 and from the second mirror 51 onto the region 42, 43 next to the couch 19, e.g. on the left or right next to the couch 19. In an embodiment, the two mirrors 50, 51 of an acquisition path 48, 49 are arranged in such a way that the couch 19 is arranged outside of the partial fields of view 45, 46, but the regions 42, 43 next to the couch 19 are fully acquired.

The second acquisition apparatus 37 also has an evaluation unit (also referred to herein as evaluation circuitry) 52, which is embodied for an evaluation of the acquired position data of the medical operator 33 (FIG. 1). The evaluation unit 52 may comprise a computing unit, e.g. a microcontroller, which is embodied for evaluation of the acquired position data of the medical operator 33. In addition, the evaluation unit 52 may comprise software, which is embodied for an evaluation of the position data of the medical operator 33 acquired by means of the sensor unit 39. In an embodiment, a position of the medical operator 33 relative to the z-direction and/or the longitudinal direction 36 of the couch 19 is ascertained and/or determined with the evaluation of the position data acquired by means of the sensor unit 39.

The second acquisition apparatus 37 has an optical data transfer unit (also referred to herein as optical data transfer circuitry) 53 for data transfer of a position of the medical operator 33. In the present exemplary embodiment, the data is transferred from the second acquisition apparatus 37 to the linear axis unit 29 by means of the optical data transfer unit 53. In an alternative embodiment the data can also be transferred to the magnetic unit 11 and/or to the system control unit 23 of the magnetic resonance apparatus 10 by means of the optical data transfer unit 53. The optical data transfer unit 53 has at least one optical fiber 54, which connects the second acquisition apparatus 37 to the linear axis unit 29 for data transfer. In an embodiment, the second acquisition apparatus 37, e.g. the evaluation unit 52 of the second acquisition apparatus 37, has a corresponding optical data interface.

The represented medical imaging apparatus 56, e.g. the magnetic resonance apparatus 10, can of course comprise further components which medical imaging apparatuses 56, e.g. magnetic resonance apparatuses 10, customarily have. A general mode of operation of a medical imaging apparatus 56, e.g. the magnetic resonance apparatus 10, is known to a person skilled in the art, moreover, so a detailed description of the further component will be omitted.

Figure 3:
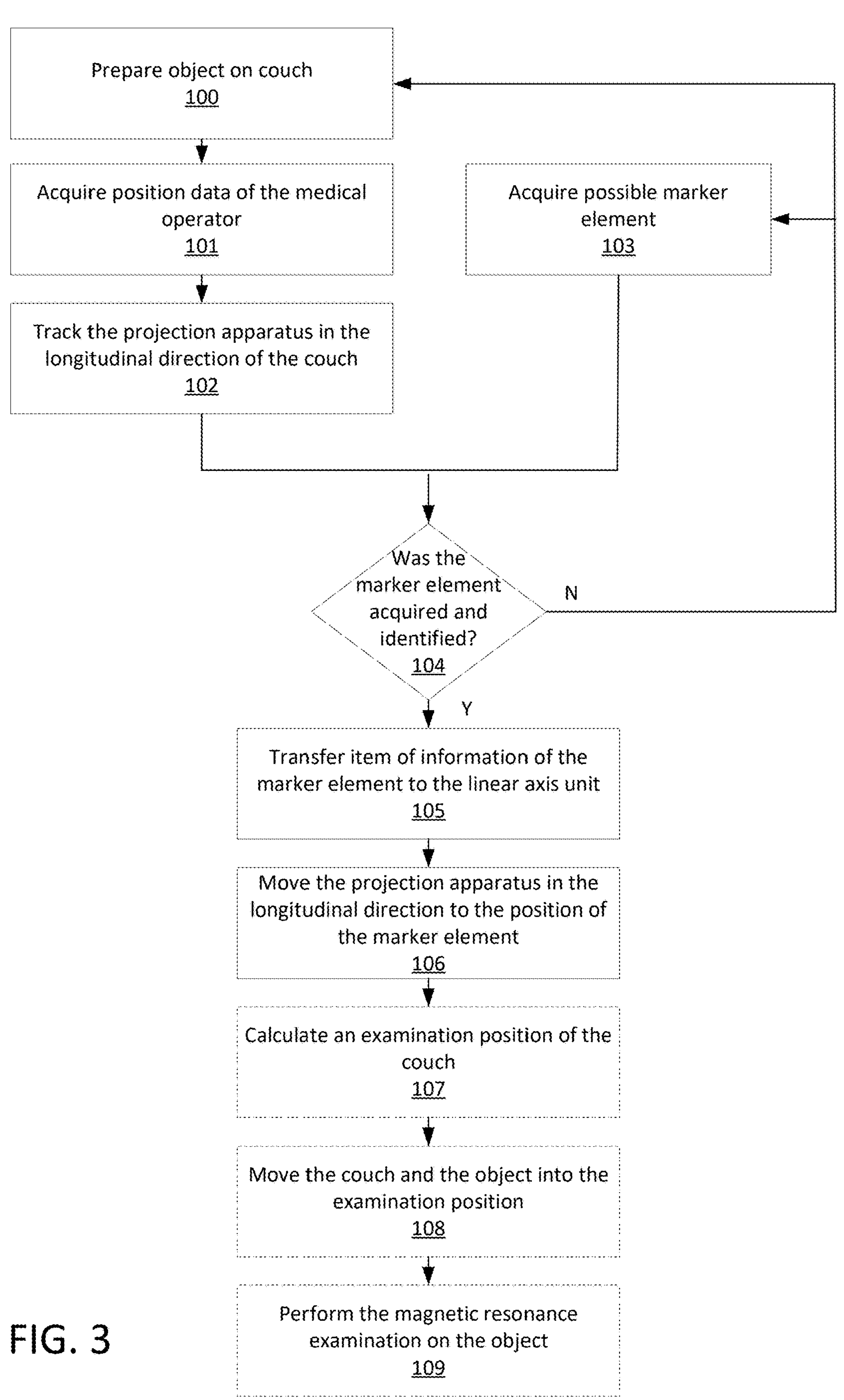
FIG. 3 illustrates an example method for acquiring a position of a region to be examined of an object by means of a first acquisition apparatus for a medical imaging examination, in accordance with one or more aspects of the present disclosure.

FIG. 3 represents a method for acquiring a position of a region to be examined of an object, e.g. of a patient 16, by means of the first acquisition apparatus 27 for a medical imaging examination, e.g. a magnetic resonance examination. For controlling the method, the medical imaging apparatus, e.g. the magnetic resonance apparatus 10, has a computing unit 55, which controls the individual method steps of the method for acquiring a position of a region to be examined of an object, e.g. of a patient 16. The computing unit 55 is encompassed by the system control unit 23 here. For this the computing unit 55 has control software and/or computer programs which are saved in a memory of the computing unit 55. When the control software and/or the computer programs is/are executed by a processor of the computing unit 55, the individual method steps are actuated accordingly.

In a first method step 100, the object is prepared on the couch 19 of the patient-supporting apparatus 17. For this, the couch 19 is located in front of the recording region 15 of the magnetic resonance apparatus 10 in a basic position. The first method step 100, e.g. preparing the object and/or the patient 16, may take place manually by way of the medical operator 33.

In a second method step 101, position data of the medical operator 33 is acquired by means of the second acquisition apparatus 37. The position data of the medical operator 33 is acquired during the manual preparation of the object, e.g. of the patient 16, on the couch 19. During acquisition of the position data of the medical operator 33 by means of the second acquisition apparatus 37 a region of the couch 19 is faded out and/or eliminated in a field of view 41 of the second acquisition apparatus 37, e.g. of the sensor unit 39 with the plurality of thermal imaging sensors 40. For this, as already described in relation to the statements relating to FIGS. 1 and 2, the field of view 41 of the second acquisition apparatus 37, e.g. of the sensor unit 39, is divided and/or deflected. In an embodiment, the field of view 41 of the sensor unit 39 is divided into two acquisition paths 48, 49 by means of the field of view manipulation unit 53, with the two acquisition paths 48, 49 acquiring the regions 42, 43 on the left and right next to the couch 19 and therewith eliminating a possible whereabouts of the medical operator 33 and the couch 19 from the field of view 41. For example, the field of view 41 of the sensor unit 39 is divided into two partial fields of view 45, 46.

In a further, third method step 102, the projection apparatus 28 is tracked in the longitudinal direction 36 of the couch 19 to a position of the medical operator 33. Tracking takes place on the basis of an item of position information of the medical operator 33 ascertained from the acquired position data. The acquired position data is evaluated by means of the evaluation unit 52, e.g. of the microcontroller, of the second acquisition apparatus 37 and a position of the medical operator 33 in respect of the longitudinal direction 36 of the couch 19 is determined. In this third method step 102, the ascertained item of position information of the medical operator 33 is then transferred to the linear axis unit 29, e.g. by means of the optical data transfer unit 53 of the second acquisition apparatus 37. The projection apparatus 28 is then tracked to the ascertained position of the medical operator 33, e.g. in the longitudinal direction 36 of the couch 19, by means of the linear axis unit 29.

At the same time as method steps 100, 101, 102 the region of the couch 19 is constantly acquired by means of the first acquisition apparatus 27 in a further method step 103 to acquire a possible marker element 34. The marker element 34 can comprise a finger of the medical operator 33 or also a hand-guided item, such as a marker bar. For this the first acquisition apparatus 27 also has corresponding software and/or computer programs in order to identify the marker element 34 in the acquired image data, e.g. camera data. The marker element 34 is positioned manually by the medical operator 33, with the marker element 34 being positioned at the region to be examined of the object, e.g. of the patient 16.

In a further method step 104, it is ascertained whether the marker element 34 was acquired and identified by the first acquisition apparatus 27 or not. If the first acquisition apparatus 27 did not acquire and identify a marker element 34, the method steps 100, 101, 102, 103 are repeated until the region to be examined of the object, e.g. of the patient 16, is defined by means of a positioning of the marker element 34.

As soon as the marker element 34 has been acquired and identified by the first acquisition apparatus 27, the position of the marker element 34 is acquired by means of the first acquisition apparatus 27 in a further method step 105. In this method step 105, an item of position information of the marker element 34 is also transferred to the linear axis unit 29 by the first acquisition apparatus 27.

In a further method step 106, firstly the projection apparatus 28 is moved in the longitudinal direction 36 of the couch 19 to the position of the marker element 34 by means of the linear axis unit 29. The projection apparatus 28 is moved from the most recently adjusted position, for instance the position of the medical operator 33 relative to the longitudinal direction of the patient table 16, to the position of the marker element 34. A feedback marking at the acquired position of the region to be examined is then projected and/or displayed by means of the projection apparatus 28.

In a further optional method step 107, an examination position of the couch 19 for the pending medical imaging examination, e.g. magnetic resonance examination, is calculated using the acquired position of the region to be examined of the object, e.g. of the patient 16. In a further optional method step 108, the couch 19, together with the object, e.g. with the patient 16, is then moved into this examination position for acquiring medical imaging data, for instance magnetic resonance data, of the region to be examined. In this examination position the region to be examined of the object, e.g. of the patient 16, is located inside the recording region 15, e.g. the isocenter, of the medical imaging apparatus 56, e.g. of the magnetic resonance apparatus 10. The medical imaging examination, e.g. the magnetic resonance examination, of the region to be examined of the object, for example of the patient 16, is then carried out in a further optional method step 109.

Although the disclosure has been illustrated and described in detail by the exemplary embodiments, it is not limited by the disclosed examples and a person skilled in the art can derive other variations herefrom without departing from the protective scope of the disclosure.

The various components described herein may be referred to as "units." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units or subunits, as applicable and relevant, may alternatively be referred to herein as "circuitry," "controllers," "processors," or "processing circuitry," or alternatively as noted herein.

Independent of the grammatical term usage, individuals with male, female or other gender identities are included within the term.

What is claimed is:

1. A medical imager, comprising:

a couch configured to receive an object positioned for a medical imaging examination and to be moved into a recording region of the medical imager;

first acquisition circuitry comprising a first sensor configured to acquire a position of a region of the object to be examined for a medical imaging examination;

a projector configured to project and/or display a feedback marking at the acquired position of the region of the object to be examined;

a linear axis positioner configured to move the projector along a longitudinal direction of the couch and independently of the couch, wherein the linear axis positioner is arranged above the couch and parallel to the longitudinal direction of the couch; and second acquisition circuitry comprising a second sensor, separate from the first sensor, the second sensor being configured to acquire position data of a medical operator during preparation of the object for the medical imaging examination, wherein the linear axis positioner is configured to use the acquired position data of the medical operator to move the projector based on a position of the medical operator such that the projector follows the medical operator during the preparation of the object for the medical imaging examination.

2. The medical imager as claimed in claim 1, wherein the medical imager comprises a magnetic resonance imaging (MRI) device.

3. The medical imager as claimed in claim 1, wherein the second sensor has a field of view that comprises a region proximate to the couch.

4. The medical imager as claimed in claim 3, wherein the second sensor comprises at least one thermal imaging sensor.

5. The medical imager as claimed in claim 3, wherein the second acquisition circuitry comprises field of view manipulation circuitry configured to fade out a region of the couch from the field of view of the second sensor.

6. The medical imager as claimed in claim 5, wherein the field of view manipulation circuitry is configured to divide and/or deflect the field of view of the second sensor into two partial fields of view.

7. The medical imager as claimed in claim 5, wherein the field of view manipulation circuitry comprises a mirror system with two acquisition paths, and wherein each acquisition path comprises at least one mirror configured to divert a respective partial field of view.

8. The medical imager as claimed in claim 1, wherein the second acquisition circuitry comprises evaluation circuitry that is configured to evaluate the acquired position data.

9. The medical imager as claimed in claim 1, wherein the second acquisition circuitry comprises a shielding housing.

10. The medical imager as claimed in claim 1, wherein the second acquisition circuitry comprises optical data transfer circuitry configured to transfer an item of position information of the medical operator to the medical imager and/or to the linear axis positioner.

11. The medical imager as claimed in claim 1, wherein the linear axis positioner is configured to move the projector based upon an item of position information ascertained using the acquired position data, the item of position information indicating a linear offset position of the medical operator along the longitudinal direction of the couch, and wherein the linear axis positioner is configured to move the projector by the linear offset position to follow the medical operator during the preparation of the object for the medical imaging examination.

12. The medical imager as claimed in claim 1, wherein the projector is moved to a position proximate to the medical operator along the longitudinal direction of the couch such that the projector has a reduced traverse path to project the feedback marking at the acquired position of the region of the object to be examined.

13. The medical imager as claimed in claim 1, wherein the second acquisition circuitry further comprises:

a mirror system having two acquisition paths, each acquisition path comprising a mirror configured to divert a respective partial field of view of the second sensor onto a respective region adjacent to the couch, and wherein the couch is excluded from the partial fields of view such that the second sensor acquires position data of the medical operator without detecting the object on the couch.

14. A method, comprising:

acquiring, via first acquisition circuitry comprising a first sensor, a position of a region of an object to be examined for a medical imaging examination via a medical imager;

positioning the object on a couch configured to be moved into a recording region of the medical imager;

acquiring, via second acquisition circuitry comprising a second sensor separate from the first sensor, position data of a medical operator during positioning of the object for the medical imaging examination;

moving, via a linear axis positioner based upon an item of position information of the medical operator ascertained using the acquired position data, a projector in a longitudinal direction of the couch, wherein the linear axis positioner is configured to use the item of position information of the medical operator to move the projector and independently of the couch based on a position of the medical operator such that the projector follows the medical operator during the positioning of the object for the medical imaging examination;

repeating the steps of positioning the object, acquiring the position data of the medical operator, and moving the projector until the region of the object to be examined is defined via a positioning of a marker element;

acquiring, via the first acquisition circuitry, a position of the marker element; and projecting and/or displaying, via a projector, a feedback marking at the acquired position of the region of the object to be examined.

15. The method as claimed in claim 14, wherein a region of the couch is faded out for acquiring the position data of the medical operator in a field of view of the second acquisition circuitry.

16. The method as claimed in claim 14, wherein a field of view of the second acquisition circuitry is divided and/or deflected for acquiring the position data of the medical operator.

17. The method as claimed in claim 14, further comprising:

evaluating, via the second acquisition circuitry, the acquired position data; and transferring, via optical data transfer circuitry, an ascertained item of position information of the medical operator to a linear axis positioner for positioning the projector.

18. The method as claimed claim 14, further comprising:

calculating an examination position of the couch using the acquired position of the region of the object to be examined.

19. The method as claimed in claim 18, wherein the couch is automatically moved into the examination position for acquisition of medical imaging data of the region of the object to be examined.

20. A non-transitory computer-readable medium having instructions stored thereon that, when executed by one or more processors, cause a medical imager to:

acquire, via first acquisition circuitry comprising a first sensor, a position of a region of an object to be examined for a medical imaging examination via a medical imager;

position the object on a couch configured to be moved into a recording region of the medical imager;

acquire, via second acquisition circuitry comprising a second sensor separate from the first sensor, position data of a medical operator during positioning of the object for the medical imaging examination;

move, via a linear axis positioner based upon an item of position information of the medical operator ascertained using the acquired position data, a projector in a longitudinal direction of the couch, wherein the linear axis positioner is configured to use the item of position information of the medical operator to move the projector independently of the couch based on a position of the medical operator such that the projector follows the medical operator during the positioning of the object for the medical imaging examination;

repeat the steps of positioning the object, acquiring the position data of the medical operator, and moving the projector until the region of the object to be examined is defined via a positioning of a marker element;

acquire, via the first acquisition circuitry, a position of the marker element; and project and/or display, via a projector, a feedback marking at the acquired position of the region of the object to be examined.

* * * * *